(12) United States Patent
Borigo et al.

(10) Patent No.: US 9,671,373 B2
(45) Date of Patent: Jun. 6, 2017

(54) SYSTEM AND METHOD FOR TESTING SHELL AND TUBE HEAT EXCHANGERS FOR DEFECTS

(71) Applicant: KOCH HEAT TRANSFER COMPANY, LP, Houston, TX (US)

(72) Inventors: Cody J. Borigo, State College, PA (US); Steven E. Owens, Bellefonte, PA (US); Joseph L. Rose, State College, PA (US); Jason K. Van Velsor, Julian, PA (US)

(73) Assignee: KOCH HEAT TRANSFER COMPANY, LP, Houston, TX (US)

( * ) Notice: Subject to any disclaimer, the term of this patent is extended or adjusted under 35 U.S.C. 154(b) by 176 days.

(21) Appl. No.: 14/212,355

(22) Filed: Mar. 14, 2014

(65) Prior Publication Data
US 2015/0260686 A1    Sep. 17, 2015

(51) Int. Cl.
| G01N 27/82 | (2006.01) |
| G01N 29/04 | (2006.01) |
| G01N 29/07 | (2006.01) |
| G01N 29/24 | (2006.01) |
| G01N 29/28 | (2006.01) |
| G01N 29/34 | (2006.01) |
| H01L 21/00 | (2006.01) |
| G06Q 10/00 | (2012.01) |
| H04R 1/00  | (2006.01) |

(52) U.S. Cl.
CPC ........... *G01N 29/043* (2013.01); *G01N 29/07* (2013.01); *G01N 29/2412* (2013.01); *G01N 29/28* (2013.01); *G01N 29/348* (2013.01); *G01N 2291/0425* (2013.01); *G01N 2291/2636* (2013.01); *G06Q 10/00* (2013.01); *H01L 21/00* (2013.01); *H04R 1/00* (2013.01)

(58) Field of Classification Search
CPC ........... H01L 21/00; H04R 1/00; G06Q 10/00
See application file for complete search history.

(56) References Cited

U.S. PATENT DOCUMENTS

| 3,357,001 A * | 12/1967 | Smith, Jr. ............ G11C 27/022 365/157 |
| 3,752,664 A * | 8/1973 | Steinemann ............ C22C 30/00 148/421 |
| 5,734,588 A | 3/1998 | Rose et al. |
| | | (Continued) |

OTHER PUBLICATIONS

Rose, J.L., Ultrasonic Waves in Solid Media. 1st ed. 1999, Cambridge, UK: Cambridge University Press. 454 pp.
(Continued)

*Primary Examiner* — Jermele M Hollington
*Assistant Examiner* — Temilade Rhodes-Vivour

(57) ABSTRACT

A magnetostrictive transducer assembly for generating a longitudinal elastic guided wave of a selected frequency and mode and for guiding the wave into an open end of a heat exchanger tube for testing the tube. The transducer assembly comprises a current-carrying coil of wire, a magnetostrictive material wrapped around the coil of wire, a mechanism for pressing the magnetostrictive material against an inner surface of the tube, and one or more biasing magnets placed in the vicinity of the current-carrying coil of wire and the magnetostrictive material.

24 Claims, 9 Drawing Sheets

(56) References Cited

U.S. PATENT DOCUMENTS

| | | | | |
|---|---|---|---|---|
| 5,892,162 | A | * | 4/1999 | Spinks .................... B06B 1/045 73/40.5 A |
| 5,970,434 | A | * | 10/1999 | Brophy .................. G01B 17/02 324/220 |
| 7,019,520 | B2 | | 3/2006 | Kwun et al. |
| 2004/0050166 | A1 | * | 3/2004 | Batzinger ............ G01N 29/069 73/614 |
| 2005/0104584 | A1 | * | 5/2005 | Kwun .................... G01N 27/82 324/238 |
| 2005/0179430 | A1 | * | 8/2005 | Park ....................... G01N 27/82 324/240 |
| 2006/0158956 | A1 | * | 7/2006 | Laugharn, Jr. .......... B01F 11/02 366/127 |
| 2008/0175416 | A1 | * | 7/2008 | Suzuki .................. H04R 15/02 381/152 |
| 2011/0116664 | A1 | * | 5/2011 | Fujioka .................. H01L 41/12 381/190 |

OTHER PUBLICATIONS

Trémolet de Lacheisserie, E., Magnetostriction: Theory and Applications of Magnetoelasticity, CRC press, 1993.

\* cited by examiner

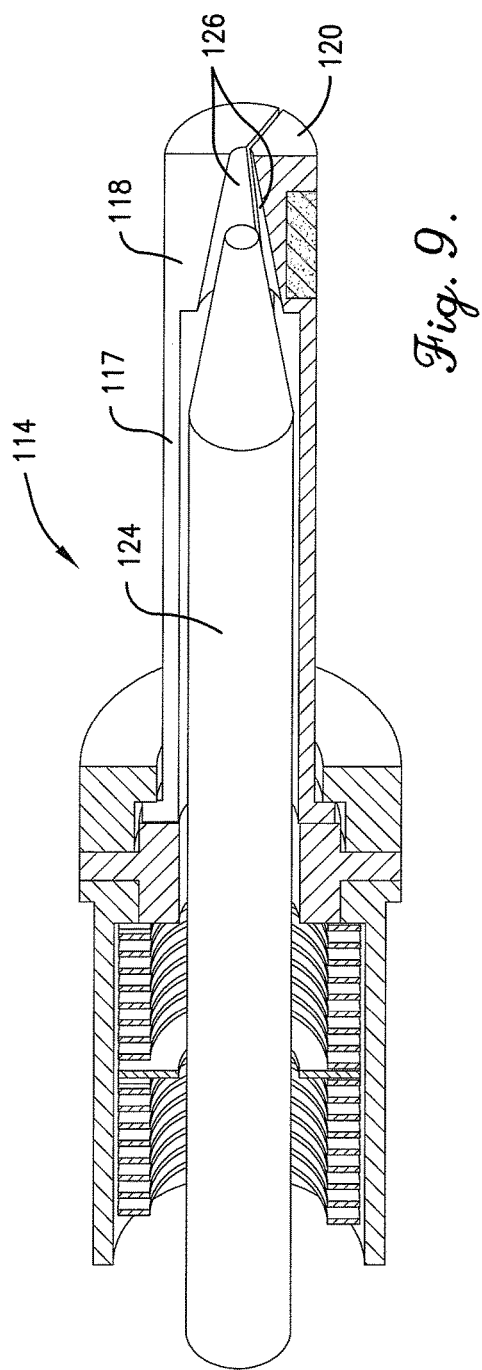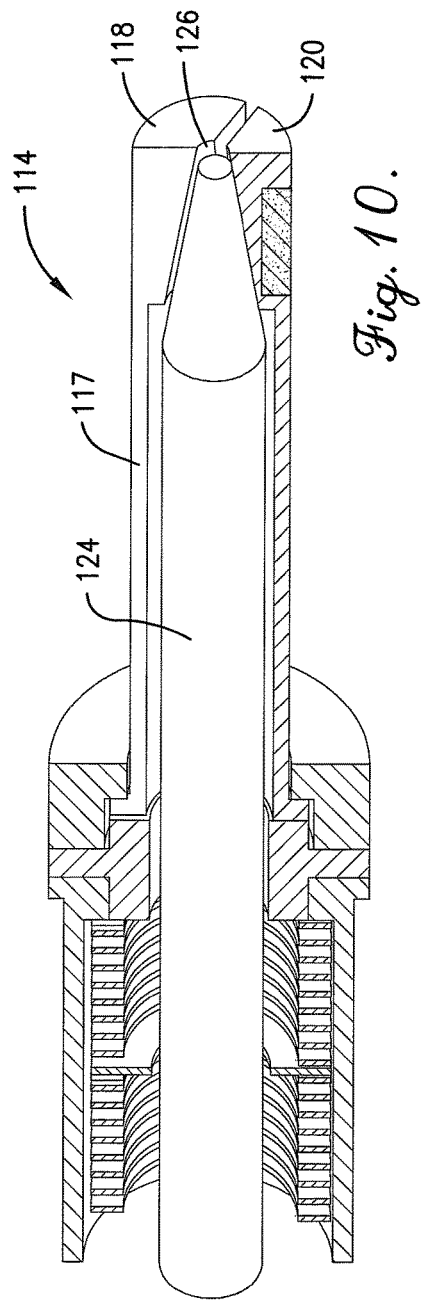

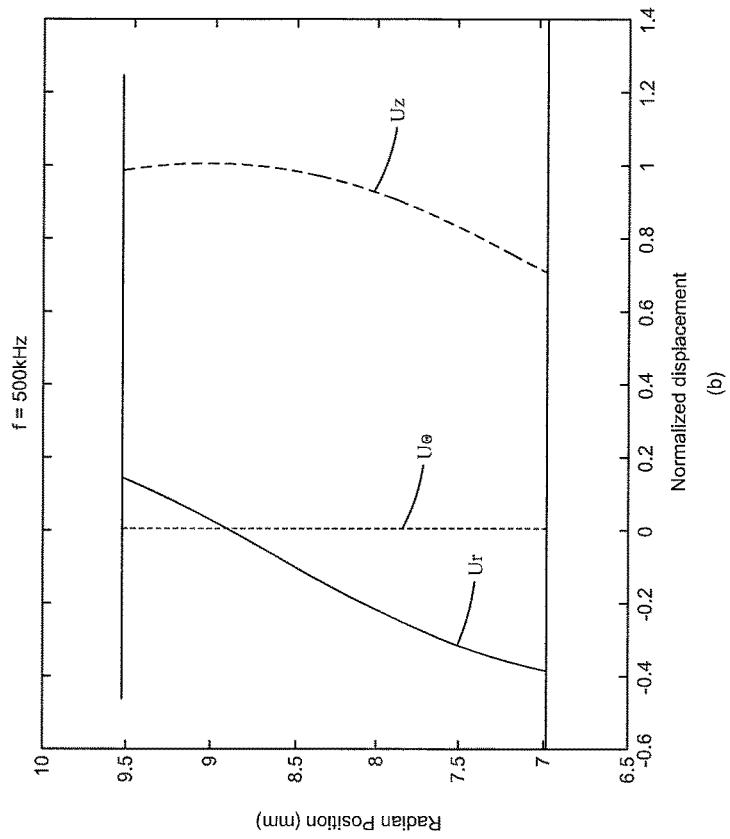
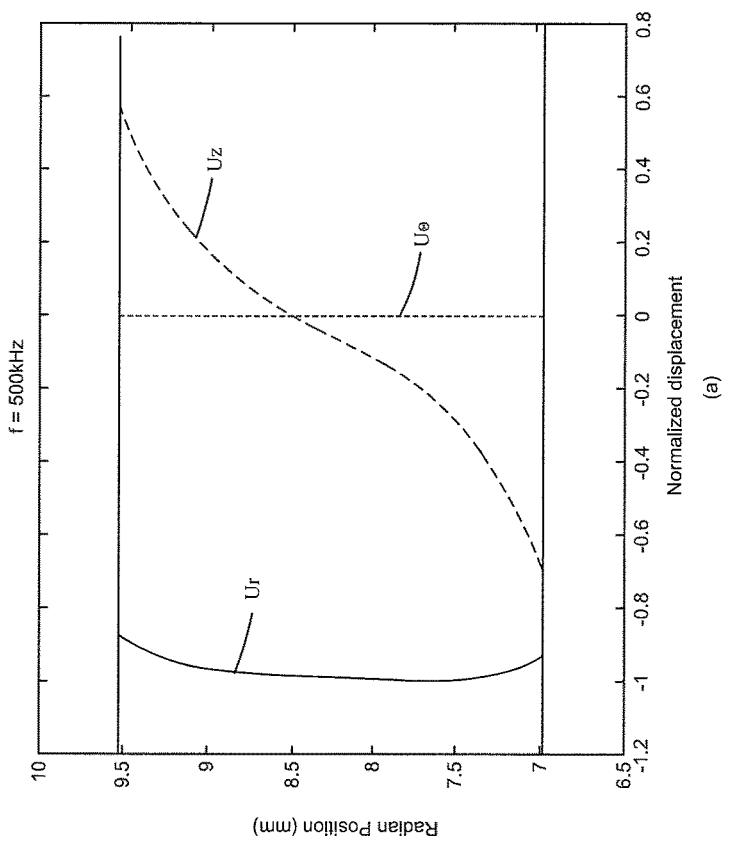
Fig. 14.

SYSTEM AND METHOD FOR TESTING SHELL AND TUBE HEAT EXCHANGERS FOR DEFECTS

BACKGROUND

Shell and tube type heat exchangers are commonly used in oil refineries, chemical process plants, and other large-scale applications because of their ability to handle high-pressure and high volume fluid flow. Such heat exchangers typically consist of a large pressure vessel or shell and a number of tubes positioned inside the shell. One fluid runs through the tubes, and another fluid runs through the shell and over the tubes to transfer heat from or to the fluid in the tubes.

A non-linear tube heat exchanger is a particular type of shell and tube heat exchanger that includes spiral-turned tubes rather than straight ones. The spiral-turned tubes produce forced vortex fluid motion and/or other fluid agitation and swirl flow to enhance their thermal efficiency and thus permit use of smaller heat exchangers when space is limited.

Heat exchangers with spiral-turned or straight tubes must be tested for defects before they are placed in service and periodically thereafter to ensure optimum performance and to prevent leakage from or into the tubes. This strict separation of fluids can be compromised by tube failure, which may be caused by corrosion, metal erosion, or cracking. Tube failure is additionally problematic because it reduces the thermal efficiency of a heat exchanger and can impede fluid flow. Therefore regular tube inspection and maintenance is desirable. Unfortunately, it is difficult and time-consuming to test shell and tube type heat exchangers, especially those with spiral-turned tubes.

SUMMARY

The present invention provides improved systems and methods for testing shell and tube type heat exchangers for defects. A method in accordance with one embodiment of the invention broadly comprises the steps of generating a longitudinal elastic guided wave of a selected frequency and mode; guiding the wave into an open end of a heat exchanger tube; sensing a reflection of the guided wave from a defect in the tube; measuring a time duration between the generation of the guided wave and the sensing of the reflection of the guided wave; and determining a location of the defect in the tube based on the measured time duration.

A key aspect of the above-described method and other embodiments of the invention is the use of selectively excited longitudinal guided waves for tube inspection rather than other types of elastic waves. Applicant experimented with various different ultrasonic waves to test for defects inside the tubes of non-linear heat exchangers but initially had difficulty in getting the waves to traverse the non-linear geometries of the tubes over long distances. Applicant then discovered that such heat exchangers could be successfully tested with ultrasonic longitudinal guided waves generated and guided in a specific manner as described in more detail below.

The present invention also provides unique transducer assemblies for implementing the above described method and other embodiments of the invention. One such transducer assembly is a magnetostrictive type transducer that generates a longitudinal elastic guided wave of a selected frequency and mode and guides the wave into an open end of a heat exchanger tube for testing the tube. The transducer assembly may comprise a current-carrying coil of wire; a magnetostrictive material wrapped around the coil of wire; biasing magnets in the vicinity of the current-carrying coil of wire and the magnetostrictive material; a probe for inserting the other components of the transducer assembly into an open end of a tube to be tested. The current-carrying coil of wire may comprise a dual-layer flexible coil made of copper-plated polymide and configured to operate at an excitation frequency of approximately 500 kHz. The current-carrying coil of wire may also comprise two separate coils that can be independently energized.

Applicant further discovered that the above-described transducer assembly operates more effectively when its magnetostrictive material is in firm contact with the spiral-turned tube in which it is positioned. Thus, embodiments of the probe may comprise a mechanism for pressing the magnetostrictive material against an inner surface of the spiral-turned tube. In one embodiment, the mechanism comprises an expandable boot or air bladder. In other embodiments, the mechanism may comprise a mechanically-actuated expander.

Applicant further discovered that the front tube sheet of shell and tube type heat exchangers can interfere with the transmission and receipt of guided waves. Thus, embodiments of the probe may have an elongated support neck for inserting the coil of wire and the magnetostrictive material a distance beyond the tube sheet to avoid interference with the tube sheet.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 9 is a vertical side sectional view of a probe that may be used to insert portions of the transducer assembly into an open end of a heat exchanger tube, with the probe shown in its retracted position.

FIG. 10 is a vertical side sectional view of the probe of FIG. 9 in its expanded position.

Figure 13:
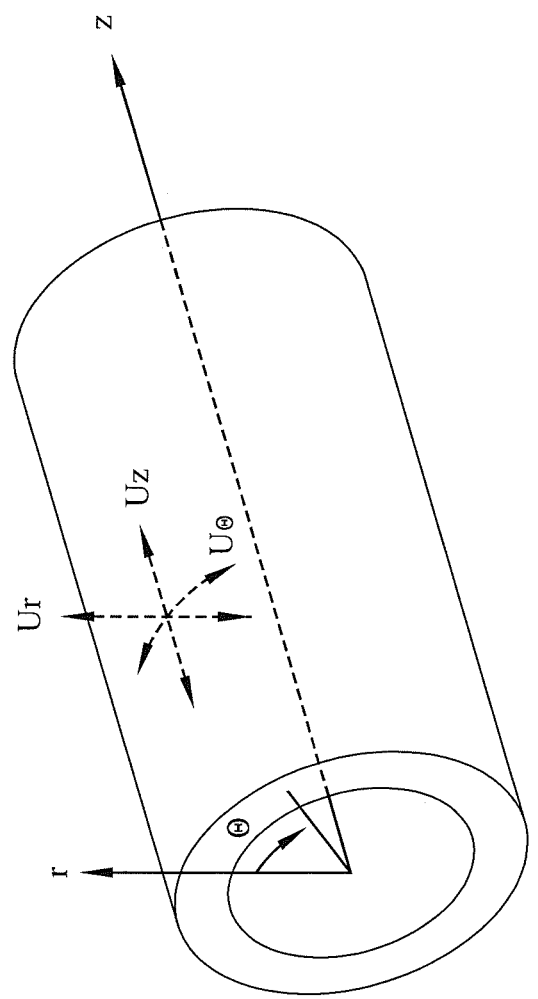

FIG. 13 identifies the displacement component orientations for a heat exchanger tube.

Figure 11:
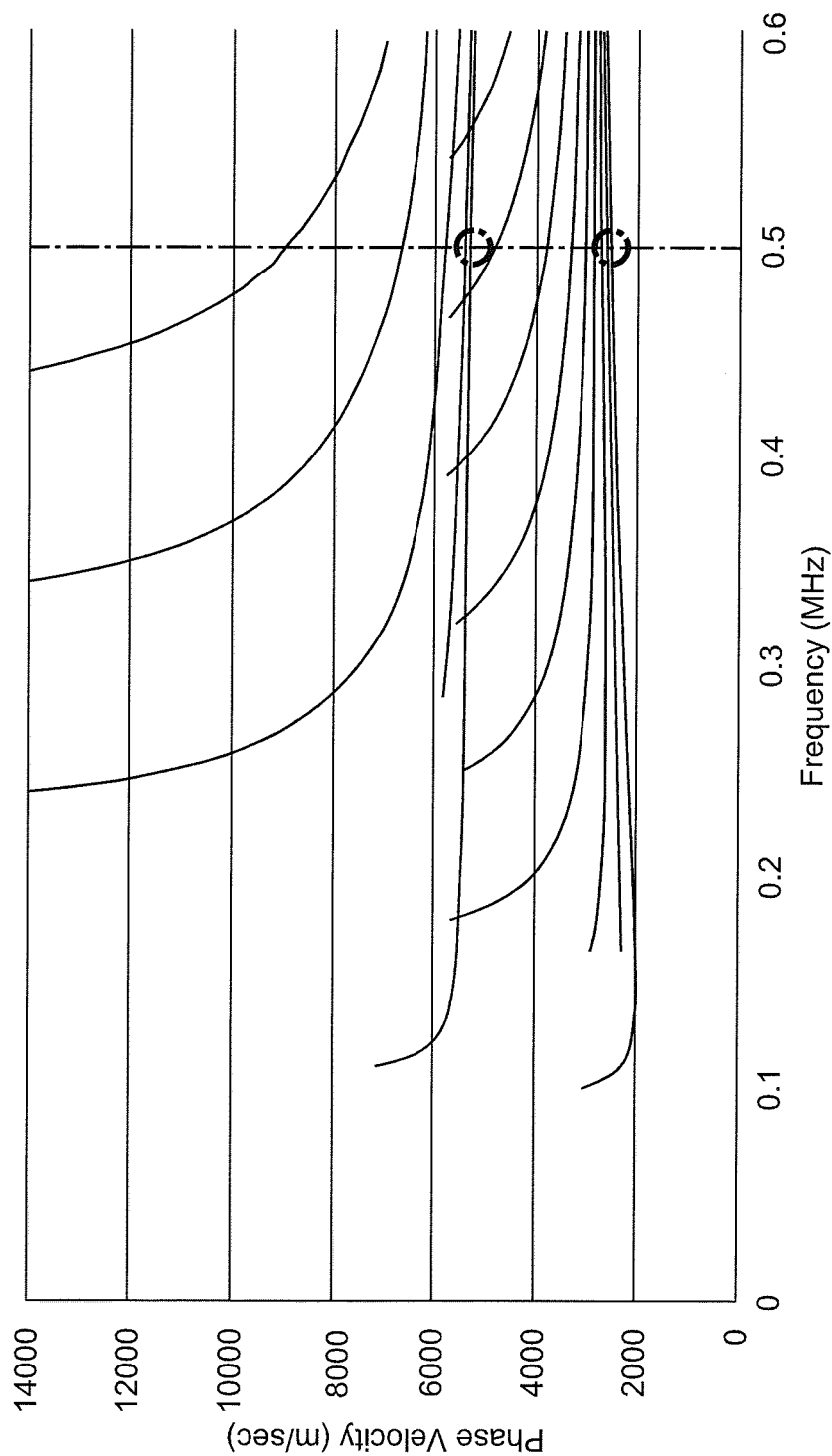
FIG. 11 is a phase velocity dispersion curve for a 0.75" OD steel heat exchanger tube with 0.1" wall thickness with the 500 kHz activation line and fundamental longitudinal modes noted.
Figure 12:
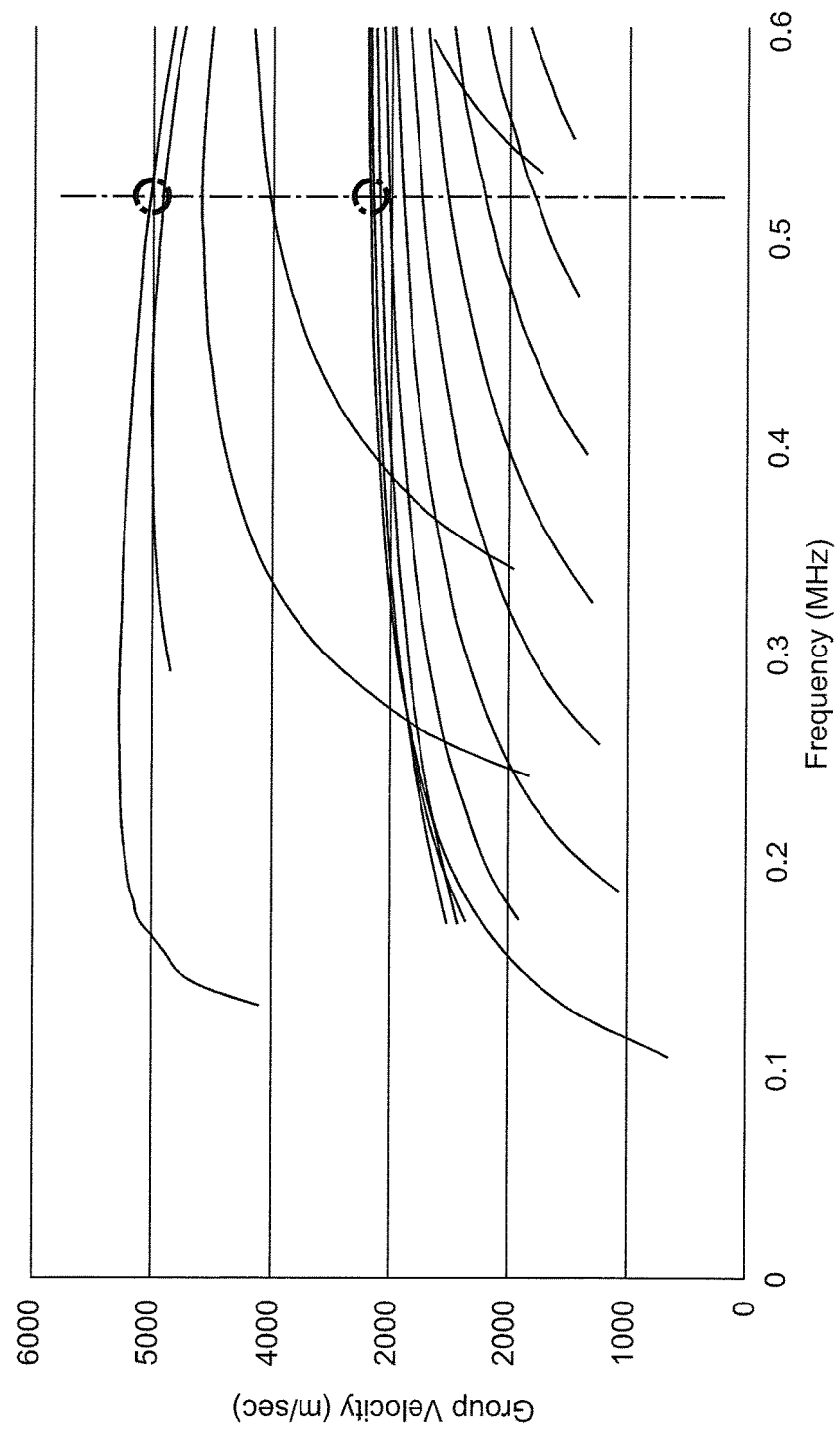
FIG. 12 is a group velocity dispersion curve for a 0.75" OD steel heat exchanger tube with 0.1" wall thickness with the 500 kHz activation line and fundamental longitudinal modes noted.

FIG. 14 illustrates the displacement wave structures through the thickness of a tube wall for the points highlighted in FIGS. 11 and 12.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
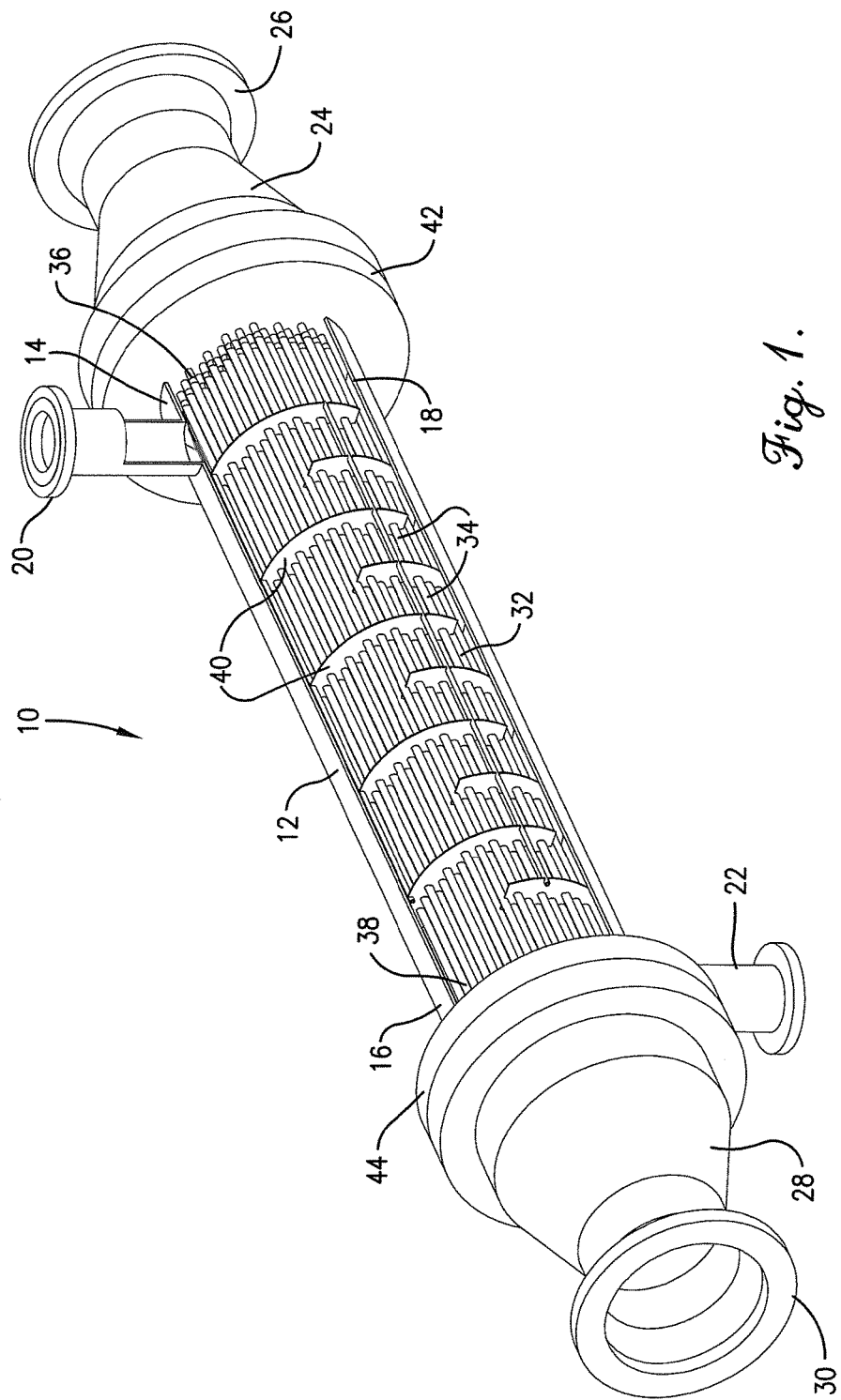
FIG. 1 is a perspective view of an exemplary shell and tube type heat exchanger that may be tested with systems and methods of the present invention, with portions of the heat exchanger broken away to show an internal tube bundle.

The present invention provides systems and methods for testing shell and tube type heat exchangers for cracks, internal protrusions, bends, corrosion, holes, and other defects. An exemplary heat exchanger that may be tested with the technology of the present invention is illustrated in FIG. 1 and represented broadly by the numeral 10. The exemplary heat exchanger 10 is a shell-and-tube heat exchanger and includes an elongated shell 12 having a front end 14, an opposed end 16, and an open interior volume 18. The shell 12 is of a generally cylindrical configuration, although it may have other shapes. The shell 12 is formed of a metal, polymer, or other material that is generally inert to the fluid within the shell 12 and is able to withstand the pressures and temperatures within the shell 12 during operation of the heat exchanger 10.

An inlet nozzle 20 extends from the shell 12 at the front end 14 for introducing a shell-side fluid into an interior volume 18 of the shell 12. An outlet nozzle 22 extends from the shell 12 for removing the shell-side fluid from the interior volume 18 of the shell 12. The outlet nozzle 22 may be positioned at the opposite end 16 of the shell 12 from the front end 14 at which the inlet nozzle 20 is positioned. The outlet nozzle 22 may also be positioned at the front end 14 with the inlet nozzle 20 and a longitudinally-extending baffle may be positioned within the interior volume 18 of the shell 12. The longitudinally-extending baffle forces the shell-side fluid to flow from the inlet nozzle 20 to the opposite end 16 of the shell 12 before reversing direction to flow on the opposite side of the baffle back to the front end 14 where it exits the interior volume 18 of the shell 12 through the outlet nozzle 22. The inlet nozzle 20 and the outlet nozzle 22 typically extend radially from the shell 12, but they may extend from the shell 12 in other orientations, such as tangentially.

The illustrated heat exchanger 10 is a single pass type exchanger with an inlet channel or head 24 defining an interior plenum. An inlet nozzle 26 for the tube-side fluid is positioned to close the open front end 14 of the shell 12. An outlet channel or head 28 defining an interior plenum and having an outlet nozzle 30 for the tube-side fluid is positioned to close the open end 16 of the shell 12.

The heat exchanger 10 may instead be a two pass tube-side type exchanger where the inlet head 24 and outlet head 28 are both positioned at the front end 14 of the shell 12 and the other end 16 of the shell is closed. The inlet nozzle 26 and outlet nozzle 30 extend along the longitudinal center axis of the shell 12 in the illustrated embodiment, but they may extend in other orientations, such as perpendicularly to the longitudinal center axis of the shell 12.

A tube bundle 32 is positioned in the open interior volume 18 of the shell 12 and comprises a plurality of hollow, elongated tubes 34 that extend in a parallel and spaced-apart relationship to each other and are positioned in a preselected pattern. Each of the tubes 34 has an open first end 36 for entry of a tube-side fluid for flow within the tube 34 along a longitudinal length of the tube 34 and an opposite open second end 38 for the first fluid to exit the tube 34. The tubes 34 may be formed from thermally-conductive, corrosion-resistant materials, such as various metals, including copper alloy, stainless steel, carbon steel, non-ferrous copper alloy, Inconel alloys, nickel, Hastelloy alloys, and titanium.

Figure 2:
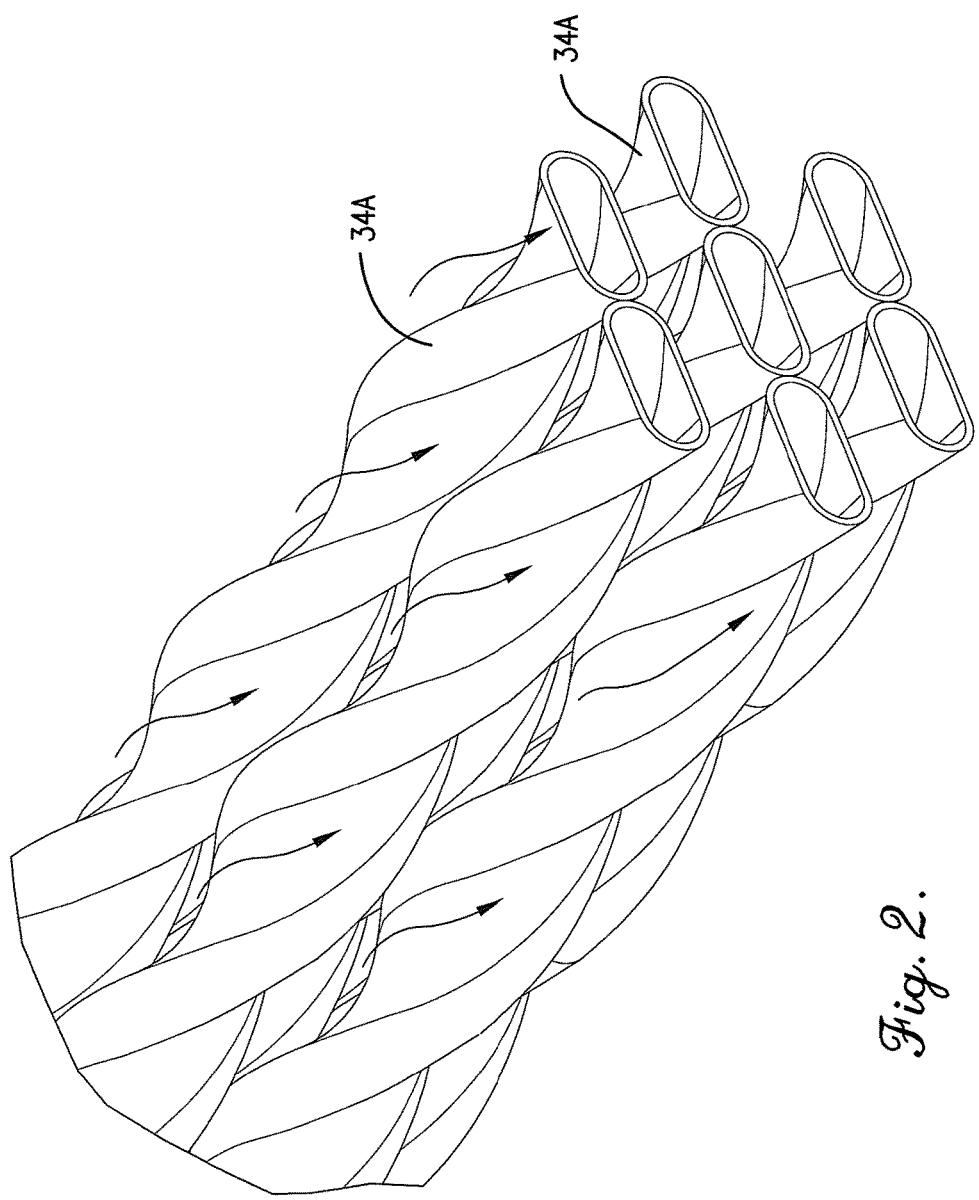
FIG. 2 is a fragmentary perspective view of a portion of a spiral-turned tube bundle of the heat exchanger.

The present invention is particularly useful for testing non-linear heat exchanger tubes such as the tubes 34A illustrated in FIG. 2. Such tubes 34A may be, for example, spiral-turned double radius oval tubes that are welded or otherwise attached by their ends to tube sheets described below. Such heat exchanger tubes produce forced vortex fluid motion and/or other fluid agitation and swirl flow to enhance their thermal efficiency to permit use of a smaller heat exchanger when space is limited.

Figure 4:
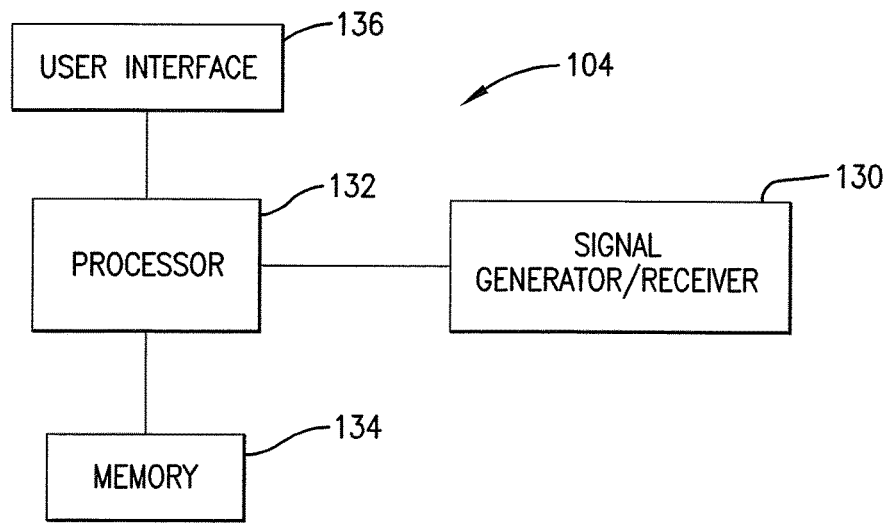
FIG. 4 is a block diagram of components of the control unit of the testing system.

Returning to FIG. 1, the tube bundle 32 may include a plurality of plate-like baffles 40 positioned at spaced apart positions along the longitudinal length of the tubes 34. The baffles 40 function to redirect the flow of the shell-side fluid as it flows exteriorly of the tubes 34. The baffles 40 also serve to support and maintain the desired positioning of the tubes 34. As best shown in FIG. 4, each of the baffles 40 has individual openings through which the tubes 34 extend. The openings are sized slightly larger than the tubes 34 to permit the tubes 34 to be longitudinally inserted through the openings while minimizing the amount of the shell-side fluid that can pass through the openings.

The tube bundle 32 also includes at least one tube sheet 42 that is positioned at the front end 14 of the shell 12 and separates the open interior volume 18 of the shell 12 from the interior plenum of the inlet head 24. The tube sheet 42 is normally disc-shaped with a perimeter that seals against the inner surface of the shell 12 in a conventional fashion. The tube sheet 42 includes a plurality of holes that extend between its opposing faces. The first ends 36 of the tubes 34 are inserted into and secured within the holes of the tube sheet 42. If the tubes 34 are U-shaped, the second ends 38 of the tubes 34 are inserted into and secured within other holes of the tube sheet 42. In the illustrated embodiment in which the tubes 34 are straight, a second tube sheet 44 is positioned at the opposite end 16 of the shell 12 and separates the open interior volume 18 of the shell 12 from the interior plenum of the outlet head 28. The second ends 38 of the tubes 34 are inserted into and secured within the holes that extend through the second tube sheet 44.

In use, shell-side fluid is introduced through the inlet nozzle 20 into the interior volume 18 within the shell 12 of the heat exchanger 10. The shell-side fluid travels through a sinusoidal path as it travels along the length of the shell and navigates through the cutouts in the baffles 40. The shell-side fluid is then removed from the interior volume 18 of the shell 12 through the outlet nozzle 22.

The tube-side fluid is introduced through the inlet nozzle 26 into the interior plenum of the inlet head 24. The tube-side fluid is then distributed to the first ends 36 of the tubes 34 and flows along the length of the tubes 34 before exiting the second ends 38 of the tubes 34. The tube-side fluid then enters the interior plenum of the outlet head 28 before exiting the heat exchanger 10 through the outlet nozzle 30. As the shell-side and tube-side fluids travel within the heat exchanger 10, heat transfer occurs from one fluid to the other.

The above-described heat exchanger tubes 34, 34A and similar tubes may be inadvertently formed with cracks, internal protrusions, bends, and other defects that inhibit fluid flow in the tubes. Likewise, the tubes may develop cracks, holes, bends, and other defects during use. The present invention provides methods and systems for testing for such defects so that detected defects can be fixed or otherwise remedied.

A method in accordance with one embodiment of the invention broadly comprises the steps of generating a longitudinal elastic guided wave of a selected frequency and mode; guiding the wave into an open end of a heat exchanger tube; sensing a reflection of the guided wave from a defect in the tube; measuring a time duration between the generation of the guided wave and the sensing of the reflection of the guided wave; and determining a location of the defect in the tube base on the measured time duration.

An important aspect of the present invention is the use of ultrasonic longitudinal guided waves of a selected mode and frequency. Applicant evaluated the dispersion of ultrasonic longitudinal waves in straight tubing and then evaluated the geometries of non-linear tubing to determine the ideal mode and frequency range for generating and guiding ultrasonic longitudinal waves in non-linear tubing. In some embodiments, the guided waves are in a frequency range between 20 kHz and 20 MHz.

Due to the dominant in-plane displacement of the longitudinal waves within certain frequency ranges, applicant discovered they are capable of propagating for long distance in spiral-turned tubes without significant mode conversion, wave deflection, or energy reflection. Applicant also determined that the longitudinal wave modes in the appropriate frequency ranges are sensitive to small defects of as little as 1.6% tube cross-sectional area (CSA), and are capable of inspecting beyond U-bends, and show minimal interaction with tube bands and at the contact points between tubes.

Applicant developed phase and group velocity dispersion curves for a number of sample heat exchanger tubes. The ends of a spiral-turned tube are not twisted, hence allowing selection of ultrasonic energy from that point into the spiral-turned tube using calculations developed for straight tubing, as shown for one example of a 0.75" OD steel tube with a 0.1" wall thickness in FIG. 11. Calculation procedures to obtain the phase and group velocity dispersion curves and appropriate wave structures in pipes and tubes can be found in many different sources.

Exemplary phase and group velocity dispersion curves for a 0.75" OD steel tube with a 0.1" wall thickness are shown in FIG. 11 and FIG. 12, in which the $L(0,1)$ and $L(0,2)$ modes at 500 kHz frequency are noted. The other modes present are higher-order flexural (i.e. non-axisymmetric) guided wave modes associated with either the fundamental $L(0,1)$ or $L(0,2)$ axisymmetric wave modes. The displacement component orientations and the wave structures corresponding to the $L(0,1)$ and $L(0,2)$ waves modes at 500 kHz in this tube are shown in FIG. 13 and FIG. 14, respectively.

At 500 kHz, the $L(0,2)$ mode has dominant in plane displacement in the $U_z$ direction compared to the out of plane component in the $U_r$ direction. At this frequency, the phase velocity is around 5500 m/sec, and the group velocity is around 5100 m/sec. From the selected point and the determined velocities, transducer assembly designs were established to efficiently excite and receive such wave modes at this frequency.

The inspection methodology employed in embodiments of the present invention is pulse-echo, in which the excited wave, upon encountering a defect in a tube, is partially reflected back to the transducer assembly, which then acts as a receiver to detect the defect. Using the known group velocity of the guided waves in the tube, the axial location of the defect can be determined.

Figure 3:
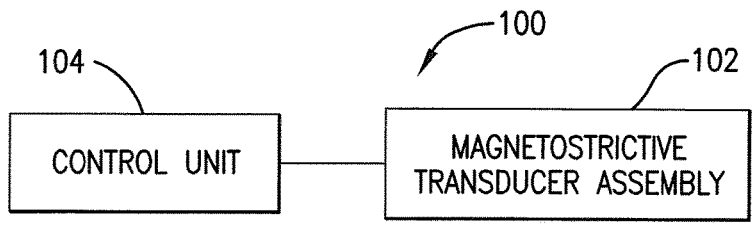
FIG. 3 is a block diagram of a testing system constructed in accordance with one embodiment of the invention.

The present invention also provides unique testing systems for implementing the above described methodology and other embodiments of the invention. A testing system 100 constructed in accordance with an embodiment of the invention is shown in FIG. 3 and broadly comprises a transducer assembly 102 and a control unit 104. The transducer assembly 102 generates longitudinal elastic guided waves of a selected frequency and mode and guides the waves into an open end of one of heat exchanger tubes 34, 34A for testing the tube. The control unit 104 includes one or more electronic components that facilitate signal generation, data acquisition, and signal processing.

The transducer assembly 102 is preferably a magnetostrictive type transducer with thin, flexible components. This allows the transducer assembly 102 to be fitted onto an expandable probe head and inserted into a heat exchanger tube as described below. Such transducer assemblies have the additional advantages of being relatively powerful and capable of exciting both longitudinal and torsional guided waves if properly designed.

Figure 5:
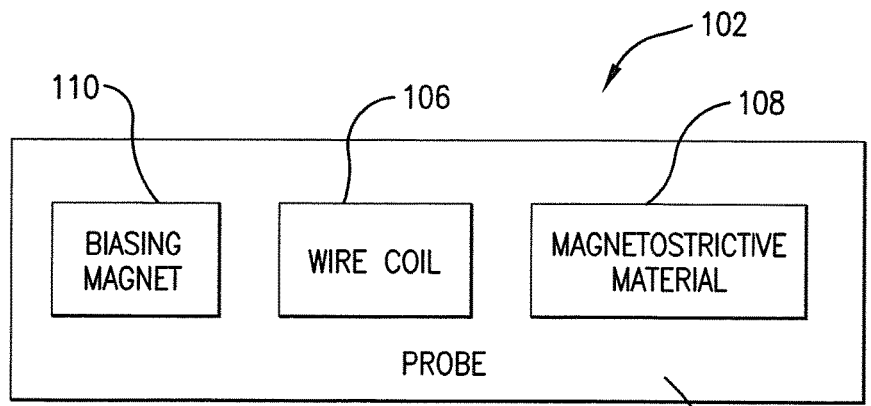
FIG. 5 is a block diagram of components of the transducer assembly of the testing system.

An embodiment of the transducer assembly 102 is illustrated in FIG. 5 and comprises a current-carrying coil of wire 106; a magnetostrictive material 108 wrapped around the coil 106; one or more biasing magnets 110, 112 placed on opposite ends of the coil 106 and the magnetostrictive material 108; and a probe 114 for inserting the coil of wire 106, magnetostrictive material 108, and biasing magnets 110 into a heat exchanger tube 34, 34A.

Figure 6:
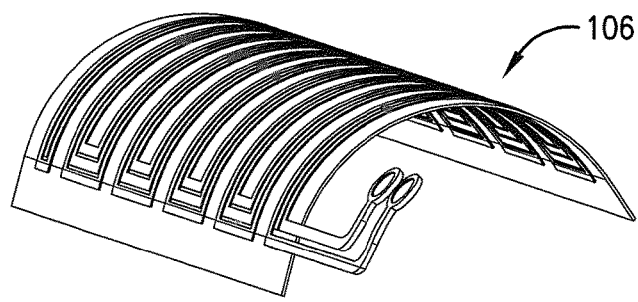
FIG. 6 is a perspective view of an embodiment of the wire coil of the transducer assembly.

In more detail, the current-carrying coil of wire 106 may comprise a dual-layer flexible coil made of copper-plated polyimide and configured to operate at an excitation frequency of approximately 500 kHz. Other embodiments of the coil may operate at excitation frequencies between 20 kHz and 20 MHz. The current-carrying coil of wire may also comprise two separate coils that can be independently energized. An exemplary coil of wire is shown in FIG. 6.

The wire coil 106 may include several comb type elements, the spacing of which is equal to the slope from the origin to the phase velocity and frequency point of the desired mode on the phase velocity dispersion curves. This spacing is equal to the wavelength of the guided wave. The group velocity allows determination of the axial distance to a defect in a tube in a pulse-echo configuration based on the travel time of the wave energy reflected from the defect.

In some embodiments, two or more wire coils 106 may be employed to achieve cancellation of the reverse-traveling wave. This is accomplished by either physically spacing the coils with a particular separation or by applying particular time delays to the signal to one of the coils in a manner that the reverse-propagating waves from both coils interact out of phase and thus superimpose to suppress one another while the forward-propagating waves superimpose to reinforce one another. Separate pulser and receiver coils may be utilized on a single probe to improve the signal-to-noise ratio and/or to reduce the uninspectable "dead zone" immediately in front of the transducer. Multiple transducer coils on a single probe also facilitate the collection of guided wave data over a greater frequency range than could be achieved with a single-coil design.

The magnetostrictive material 108 is placed over the coil 106 and converts magnetic energy created by the interaction of the coil 106 and the permanent magnets 110 to kinetic energy that excites guided waves in a heat exchanger tube 34, 34A. The magnetostrictive material 108 may be FeCo (iron cobalt) or Ni (nickel). The guided waves are generated by an interaction of the static biasing magnetic field from the biasing magnets 110 and the alternating magnetic field induced by the current-carrying traces on the wire coil 106.

The biasing magnets 110 are preferably permanent magnets but may also be electromagnets. The size and design of the magnets 110 and the coil 106 determines the guided wave modes and frequencies that can be generated by the transducer assembly and detected by the control unit 104.

During wave generation, the magnetostrictive material 108 undergoes a time-varying strain in accordance with the frequency of the signal sent to the wire coil 106. This strain, if coupled properly to the inner diameter of a tube 34, 34A, will excite guided waves in the tube, which will propagate and subsequently generate reflected wave energy upon interaction with defects in the tube. These reflected waves propagate back toward the transducer assembly 102 and, if the transducer assembly is coupled properly to the tube wall, will induce a strain in the magnetostrictive material 108 that will subsequently induce a current in the wire coil 106 that is detected by the control unit 104 or other inspection system.

Figure 7:
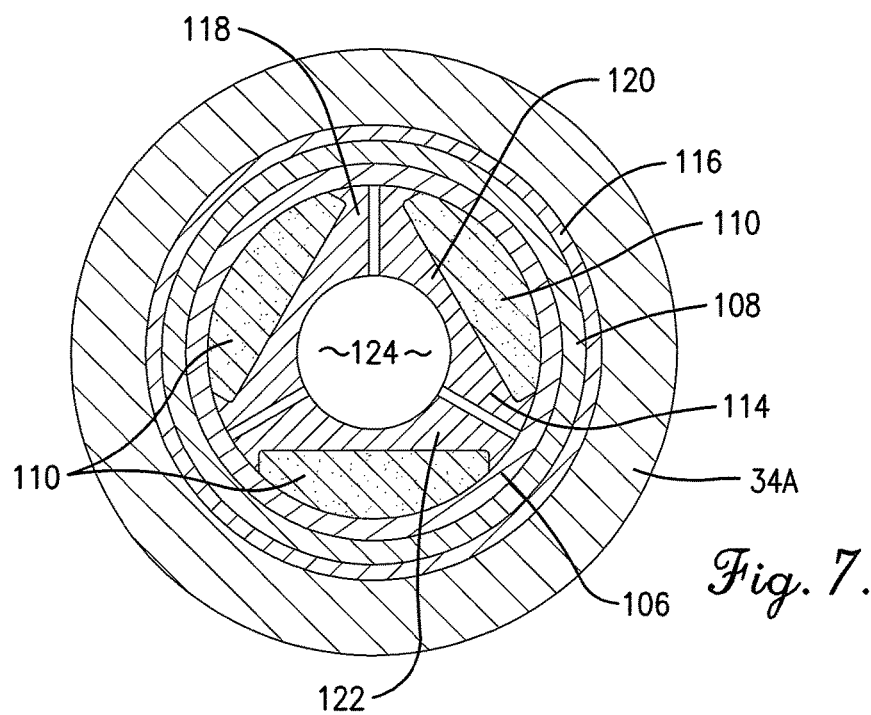
FIG. 7 is a front view looking into a heat exchanger tube showing one embodiment of the transducer assembly inside the heat exchanger tube.
Figure 8:
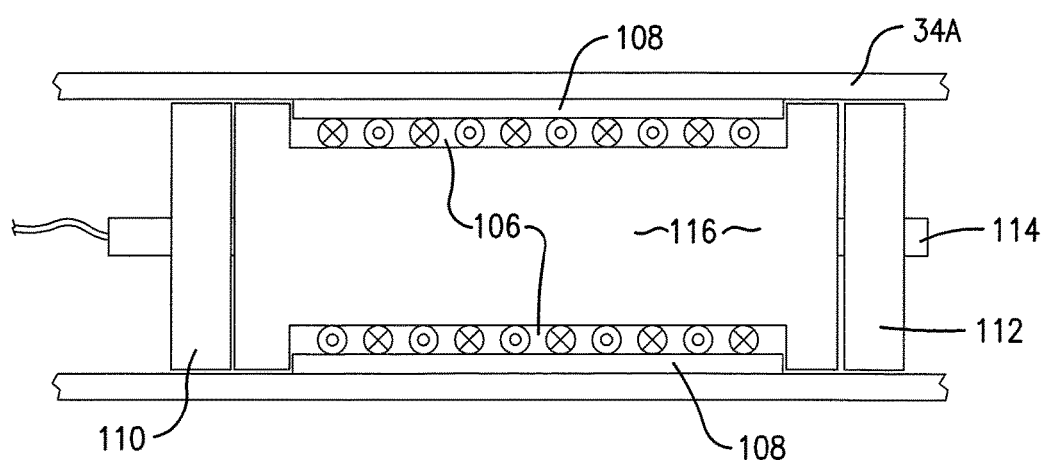
FIG. 8 is a vertical side sectional view of a heat exchanger tube showing one embodiment of the transducer assembly shown inside the heat exchanger tube.

The invention also requires proper alignment of the biasing magnets 110, wire coil 106, and magnetostrictive material 108, particularly at the edges of the latter two. If proper alignment is not achieved, the signal-to-noise ratio is reduced and the uninspectable "dead zone" in front of the transducer is enlarged. These effects are due to unintended excitation of non-axisymmetric flexural waves and/or circumferential waves. Thus, the probe 114 ensures that the other components of the transducer assembly are properly aligned and positioned within a tube 34, 34A as shown in FIGS. 7 and 8.

Due to the dominant in-plane axial displacement component of the longitudinal wave modes and the orientation and location of the probe 114 inside the tube, shear coupling is required between the magnetostrictive material 108 and the inner diameter of the tube 34, 34A. This coupling may be achieved with sufficient mechanical pressure, viscous shear couplant, a dry couplant such as neoprene, or a combination of these methods. Mechanical coupling alone may be sufficient for guided wave excitation and detection, but the addition of a shear couplant 116 shown in FIG. 7 substantially improves the signal-to-noise ratio and the repeatability and reliable of the inspection results.

The above-described shear coupling may also be achieved mechanically with a mechanism for pressing the magnetostrictive material 108 against an inner surface of the spiral-turned tube 34A. One such mechanism comprises an expandable boot or air bladder 116 as shown in FIG. 8. The boot or air bladder may be formed in nitrile tubing or other materials.

In other embodiments, the probe 114 may be configured to expand to facilitate mechanical coupling of the magnetostrictive material 108 to the tube wall so as to achieve the above-described shear coupling. This probe configuration also allows for ease of insertion and removal of the probe from tubes of various inner diameters.

An embodiment of an expandable probe 114 is shown in FIGS. 7, 9, and 10 and includes a neck 117 on which the wire coil 106, magnetostrictive material 108, and biasing magnets 110 may be placed. The neck includes three sections 118, 120, 122 that can be shifted by a shiftable tapered rod 124 between a retracted or unexpanded position shown in FIG. 9 and an expanded position shown in FIG. 10. The inner surfaces of the clamp sections 118, 120, 122 have tapered walls 126 that mate with a tapered end of the rod 124. When the rod 124 is moved forward (from left to right from the perspective of FIGS. 9 and 10), it pushes the sections 118, 120, 122 outwardly to press the magnetostrictive material 108 and wire coil 106 against the inside of the tube 34, 34A. Conversely, when the rod is moved rearward (right to left in FIGS. 9 and 10), it allows the sections 118, 120, 122 to retract so that the probe may be removed from the tube. The movement of the tapered rod may be provided by various means, including but not limited to, hydraulic, pneumatic, electric, or mechanical actuators. In order to easily retract the expanded probe, a return mechanism may be included in the probe, such as a return spring.

Applicant further discovered that the front tube sheet 42 of the heat exchanger 10 can interfere with the transmission and receipt of guided waves. Thus, the support neck 117 may be several inches long for inserting the coil of wire 106 and the magnetostrictive material 108 a distance beyond the tube sheet 42 to avoid such interference. In one embodiment, the support neck is approximately 12 inches long.

In some embodiments of the invention, the probe 114 may be designed with an interchangeable head to which the other components of the transducer assembly may be affixed. The benefit of such interchangeable heads is that they would more easily allow for the inspection of a wide range of tube sizes.

In another embodiment, an electrothermal heater may be incorporated into the probe 114 to allow for heating of the couplant 116 to control its viscosity and facilitate probe extraction in cold conditions. The heater may be a resistive heating coil printed on a flexible PCB circuit or any other type of heater.

The control system 104 controls operation of the transducer assembly 102 and detects and analyzes waves reflected from defects in the tube. As shown in FIG. 4, one embodiment of the control system includes a signal generator/receiver 130, a processor 132, memory 134, and a user interface 136.

The signal generator/receiver 130 generates the signals delivered to the wire coil 106 used to create the guided elastic waves. The signal generator/receiver also senses signals created by the wire coil 106 as a result of reflections of the guided waves. The signal generator/receiver 130 may include any conventional electronics capable of generating the required signals.

The processor 132 controls the signal generator/receiver 130 and measures the time duration between the generation of a guided wave and the receipt of a reflection to determine the location of defects in the tube. The processor may be part of a custom control device or may be a component of a conventional computer.

The user interface 136 allows an operator to initiate a testing procedure and control the processor 132 and may include any conventional buttons, switches, touchscreen displays, etc. The control system 104 may also include, or be coupled with, a display for displaying results of a heat exchanger testing procedure.

The control system 104 may employ frequency sweeping to gather ultrasonic guided wave data over a range of frequencies so that a fast-frequency analysis color map may be generated to aid an inspector in signal interpretation and improve the probability of detection for certain defects.

Aspects of the invention may be implemented with one or more computer programs stored in or on the memory 134 or other memory residing on or accessible by the processor 132. Each computer program preferably comprises an ordered listing of executable instructions for implementing logical functions in the processor. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A method of testing a heat exchanger tube for defects, the method comprising:
    generating a longitudinal elastic guided wave of a selected frequency and mode with a magnetostrictive transducer assembly;
    guiding the elastic guided wave into an open end of the tube;
    sensing a reflection of the elastic guided wave from a defect in the tube;
    measuring a time duration between generation of the elastic guided wave and the sensing of the reflection of the elastic guided wave; and
    determining a location of the defect in the tube based on the measured time duration, wherein the longitudinal elastic guided wave is generated with a magnetostrictive transducer assembly placed in the open end of the tube, the magnetostrictive transducer assembly comprising a current-carrying coil of wire, a magnetostrictive material wrapped around the coil of wire, a mechanism for pressing the magnetostrictive material against an inner surface of the tube, and one or more biasing magnets placed in the vicinity of the current-carrying coil of wire and the magnetostrictive material.

2. The method as set forth in claim 1, wherein a frequency and mode of the guided wave is selected according to a characteristic of the tube, and wherein the selected frequency and mode of the longitudinal guided wave are generated by specially-designed transducers.

3. The method as set forth in claim 1, wherein the mechanism for pressing the magnetostrictive material against an inner surface of the tube comprises an expandable boot or air bladder.

4. The method as set forth in claim 1, wherein the mechanism for pressing the magnetostrictive material against an inner surface of the tube comprises a probe with a mechanically-actuated expander.

5. The method as set forth in claim 1, wherein the current-carrying coil of wire comprises a dual-layer flexible coil made of copper-plated polyimide and configured to operate at an excitation frequency of approximately 500 kHz.

6. The method as set forth in claim 1, wherein the current-carrying coil of wire comprises two separate coils that can be independently energized.

7. The method as set forth in claim 1, wherein the magnetostrictive material comprises a strip of iron cobalt material.

8. The method as set forth in claim 1, wherein guided wave data is collected and analyzed over a range of frequencies.

9. A transducer assembly for generating a longitudinal elastic guided wave of a selected frequency and mode and for guiding the wave into an open end of a heat exchanger tube for testing the tube for defects, the transducer assembly comprising:
    a current-carrying coil of wire,
    a magnetostrictive material wrapped around the coil of wire,
    a mechanism for pressing the magnetostrictive material against an inner surface of the tube, and
    one or more biasing magnets placed in the vicinity of the current-carrying coil of wire and the magnetostrictive material.

10. The transducer assembly as set forth in claim 9, wherein the mechanism for pressing the magnetostrictive material against an inner surface of the tube comprises an expandable boot or air bladder formed of nitrile tubing.

11. The transducer assembly as set forth in claim 9, wherein the mechanism for pressing the magnetostrictive material against an inner surface of the tube comprises a mechanically-actuated expander.

12. The transducer assembly as set forth in claim 9, wherein the current-carrying coil of wire comprises a dual-layer flexible coil made of copper-plated polyimide and configured to operate at an excitation frequency of approximately 500 kHz.

13. The transducer assembly as set forth in claim 9, wherein the current-carrying coil of wire comprises two separate coils that can be independently energized.

14. The transducer assembly as set forth in claim 9, wherein the magnetostrictive material comprises a strip of iron cobalt material.

15. The transducer assembly as set forth in claim 9, wherein the transducer assembly further comprises an elongated support neck for inserting the current-carrying coil of wire and the magnetostrictive material a distance within the open end of the tube.

16. The transducer assembly as set forth in claim 9, wherein the transducer assembly includes a heating unit.

17. The transducer assembly as set forth in claim 9, wherein the transducer assembly comprises one or more interchangeable transducer assembly heads having various dimensions and transducer design characteristics.

18. A system for testing a spiral-turned tube of a heat exchanger for defects, the system comprising:
  a magnetostrictive transducer assembly for generating a longitudinal elastic guided wave of a selected frequency and mode and for guiding the wave into an open end of the spiral-turned tube, the transducer assembly comprising—
    a current-carrying coil of wire,
    a magnetostrictive material wrapped around the coil of wire,
    a mechanism for pressing the magnetostrictive material against an inner surface of the spiral-turned tube, and
    one or more biasing magnets placed in the vicinity of the current-carrying coil of wire and the magnetostrictive material; and
  a control unit for sensing a reflection of the elastic guided wave from a defect in the spiral-turned tube and for measuring a time duration between generation of the guided wave and sensing of the reflection of the guided wave for determining a location of the defect in the spiral-turned tube base on the measured time duration.

19. A method of testing a heat exchanger tube for defects, the method comprising:
  generating a longitudinal elastic guided wave of a selected wavelength with a magnetostrictive transducer assembly;
  guiding the elastic guided wave into an open end of the tube;
  sensing a reflection of the elastic guided wave from a defect in the tube;
  measuring a time duration between generation of the elastic guided wave and the sensing of the reflection of the elastic guided wave; and
  determining a location of the defect in the tube based on the measured time duration, wherein the longitudinal elastic guided wave is generated with a magnetostrictive transducer assembly placed in the open end of the tube, the magnetostrictive transducer assembly comprising a current-carrying coil of wire, a magnetostrictive material wrapped around the coil of wire, a mechanism for pressing the magnetostrictive material against an inner surface of the tube, and one or more biasing magnets placed in the vicinity of the current-carrying coil of wire and the magnetostrictive material.

20. The method as set forth in claim 19, wherein the selected wavelength is 11 mm.

21. A transducer assembly for generating a longitudinal elastic guided wave of a selected wavelength and for guiding the wave into an open end of a heat exchanger tube for testing the tube for defects, the transducer assembly comprising:
  a current-carrying coil of wire,
  a magnetostrictive material wrapped around the coil of wire,
  a mechanism for pressing the magnetostrictive material against an inner surface of the tube, and
  one or more biasing magnets placed in the vicinity of the current-carrying coil of wire and the magnetostrictive material.

22. The system as set forth in claim 21, wherein said current-carrying coil of wire is configured to generate and sense said guided waves having a wavelength of 11 mm.

23. A system for testing a spiral-turned tube of a heat exchanger for defects, the system comprising:
  a magnetostrictive transducer assembly for generating a longitudinal elastic guided wave of a selected wavelength and for guiding the wave into an open end of the spiral-turned tube, the transducer assembly comprising—
    a current-carrying coil of wire,
    a magnetostrictive material wrapped around the coil of wire,
    a mechanism for pressing the magnetostrictive material against an inner surface of the spiral-turned tube, and
    one or more biasing magnets placed in the vicinity of the current-carrying coil of wire and the magnetostrictive material; and
  a control unit for sensing a reflection of the elastic guided wave from a defect in the spiral-turned tube and for measuring a time duration between generation of the guided wave and sensing of the reflection of the guided wave for determining a location of the defect in the spiral-turned tube base on the measured time duration.

24. The system as set forth in claim 23, wherein said current-carrying coil of wire is configured to generate and sense said guided waves having a wavelength of 11 mm.

* * * * *